US012616799B2

(12) United States Patent
Haller et al.

(10) Patent No.: US 12,616,799 B2
(45) Date of Patent: May 5, 2026

(54) METHOD AND DEVICE FOR CHECKING AN ADHESIVE CONNECTION BETWEEN A HOLLOW NEEDLE OR CANNULA AND A HOLDING PART

(71) Applicant: ATS Automation Tooling Systems GmbH, Urbach (DE)

(72) Inventors: Florian Haller, Winnenden (DE); Roland Lindner, Winnenden (DE)

(73) Assignee: ATS Automation Tooling Systems GmbH, Urbach (DE)

( * ) Notice: Subject to any disclaimer, the term of this patent is extended or adjusted under 35 U.S.C. 154(b) by 1125 days.

(21) Appl. No.: 17/665,913

(22) Filed: Feb. 7, 2022

(65) Prior Publication Data

US 2022/0249782 A1     Aug. 11, 2022

(30) Foreign Application Priority Data

Feb. 8, 2021    (DE) ..................... 10 2021 102 830.2

(51) Int. Cl.
   *G06K 9/00*        (2022.01)
   *A61M 5/32*        (2006.01)
   (Continued)

(52) U.S. Cl.
   CPC ............. *A61M 5/32* (2013.01); *G06T 7/0012* (2013.01); *G06T 7/62* (2017.01); *A61M 2205/13* (2013.01);
   (Continued)

(58) Field of Classification Search
   None
   See application file for complete search history.

(56) References Cited

U.S. PATENT DOCUMENTS 5,030,833 A    7/1991  Nozaka et al.
6,461,326 B1 * 10/2002  Yang ................. A61M 25/1034
                                        250/461.1
(Continued)

FOREIGN PATENT DOCUMENTS

CN        205920065 U    2/2017
CN        210514110 U    5/2020
   (Continued)

OTHER PUBLICATIONS

Jaworski et al., "LED-generated UV for adhesive curing in medical devices" (Year: 2019).*
(Continued)

*Primary Examiner* — S J Park
(74) *Attorney, Agent, or Firm* — FLYNN THIEL, P.C.

(57)                    ABSTRACT

A method is described for checking an adhesive connection between a hollow needle or cannula of a medical syringe and a holding part, wherein the hollow needle or cannula is inserted with play in a holding portion of the holding part, and an intermediate space between the hollow needle or cannula and the holding portion is at least partially filled with an adhesive body. The adhesive body is detected by means of an optical detection device in the form of a camera, and the detection device transmits image data relating to the adhesive body to an evaluation unit in which the data are evaluated. The ACTUAL volume and/or the ACTUAL configuration of the adhesive body is determined from the image data of the adhesive body and compared with a TARGET volume and/or a TARGET configuration of the adhesive body.

10 Claims, 3 Drawing Sheets

(51) Int. Cl.
    *G06T 7/00*        (2017.01)
    *G06T 7/62*        (2017.01)

(52) U.S. Cl.
    CPC ................ *A61M 2205/3313* (2013.01); *G06T 2207/10064* (2013.01)

(56) References Cited

U.S. PATENT DOCUMENTS

| | | |
|---|---|---|
| 8,998,853 B2 | 4/2015 | Hoppe et al. |
| 2018/0001611 A1 | 1/2018 | Lingier et al. |

FOREIGN PATENT DOCUMENTS

| | | | |
|---|---|---|---|
| DE | 3890059 | T1 | 1/1989 |
| DE | 10244819 | A1 | 4/2004 |
| DE | 10257567 | A1 | 7/2004 |
| DE | 102010045095 | A1 | 3/2012 |
| DE | 102012222377 | A1 | 7/2014 |
| DE | 102013220601 | A1 | 4/2015 |
| DE | 202016103570 | U1 | 11/2017 |
| DE | 102017101228 | A1 | 7/2018 |
| EP | 1985676 | A1 | 10/2008 |
| EP | 2033673 | A1 | 3/2009 |
| EP | 3182101 | A1 | 6/2017 |

OTHER PUBLICATIONS

Tavakoli et al., "A review of adhesive bonding techniques for joining medical materials" (Year: 2005).*
Search Report issued in corresponding European Application No. 22155347.2, with English translation of categories of cited documents, dated Jun. 15, 2022 (10 pages).
German Search Report issued in corresponding German Application No. 10 2021 102 830.2, date of mailing Nov. 11, 2021 (6 pages).

* cited by examiner

METHOD AND DEVICE FOR CHECKING AN ADHESIVE CONNECTION BETWEEN A HOLLOW NEEDLE OR CANNULA AND A HOLDING PART

CROSS-REFERENCE TO RELATED APPLICATION

This claims priority from German Application No. 10 2021 102 830.2, filed Feb. 8, 2021, the disclosure of which is hereby incorporated by reference in its entirety.

FIELD OF THE INVENTION

The invention relates to a method for checking an adhesive connection between a hollow needle or cannula and a holding part, wherein the hollow needle or cannula is inserted with play in a holding portion of the holding part, and an intermediate space between the hollow needle or cannula and the holding portion is at least partially filled with an adhesive body.

In addition, the invention relates to a corresponding device for checking the adhesive connection between a hollow needle or cannula and the holding part.

BACKGROUND OF THE INVENTION

A prefabricated hollow needle or cannula for a medical syringe is glued into a tubular holding part made of glass or plastics material for the attachment thereof. The holding part can be an integral part of the syringe body, but it is also possible for the holding part to be placed on the syringe body and clamped or latched there, for example.

A hollow needle or cannula is usually an inherently stable, straight tube made of stainless steel or plastics material. The holding part has a tubular holding portion, the inside diameter of which is larger than the outside diameter of the hollow needle or cannula. When the hollow needle or cannula is inserted into the tubular holding portion of the holding part, an intermediate space remains between the outside of the hollow needle or cannula and the inner wall of the holding portion. An adhesive is filled into this intermediate space from the outside, which adhesive connects adhesively to the outer surface of the hollow needle or cannula on the one hand and to the inner wall of the holding portion on the other hand.

When using a medical syringe, it must be ensured that the hollow needle or cannula cannot become detached from the holding part. It is therefore known to check the adhesive connection between the hollow needle or cannula and the holding part by fixing the holding part and exerting a tensile force on the hollow needle or cannula, which tensile force acts on the adhesive connection. There is a risk that the tensile force will damage the adhesive connection, so that the hollow needle or cannula can become detached from the holding part when the syringe is used.

SUMMARY OF THE INVENTION

The object of the invention is to provide a method for checking an adhesive connection between a hollow needle or cannula and a holding part, with which method an assessment of the adhesive connection can take place reliably and non-destructively.

In addition, a corresponding device for checking the adhesive connection is to be created.

According to the invention, this object is achieved with regard to an embodiment of the method as disclosed herein. In this case, the adhesive body is detected by means of an optical detection device. The data relating to the adhesive body detected by the detection device are sent to an evaluation unit in which the data are evaluated. The detection device is a camera that is used to generate image data of the adhesive body.

A glass body or a glass syringe is preferably used as the holding part.

The ACTUAL volume and/or the ACTUAL configuration of the adhesive body is determined or calculated from the image data of the adhesive body. From the ACTUAL volume and/or the ACTUAL configuration of the adhesive body, conclusions can be drawn about the contact area between the adhesive body and the hollow needle or cannula and also about the size of the contact area between the adhesive body and the inner wall of the holding portion of the holding part, from which the force to be transmitted and thus the stability of the adhesive connection can in turn be derived. Furthermore, the axial penetration depth of the adhesive into the intermediate space between the hollow needle or cannula and the wall of the holding part can be determined. Furthermore, any air inclusions in the adhesive body can be determined.

The ACTUAL volume and/or the ACTUAL configuration of the adhesive body are compared in the evaluation unit with a TARGET volume and/or a TARGET configuration of the adhesive body. If there is a discrepancy between the ACTUAL volume and the TARGET volume and/or a discrepancy between the ACTUAL configuration and the TARGET configuration outside of specified limits, the adhesive connection is classified as insufficient and sorted out from the rest of the production process. In addition or as an alternative to this, the amount of adhesive for the future adhesive bodies can be adjusted, i.e. increased and/or decreased, on the basis of the detected image data.

The reliability of the method substantially depends on the quality of the data that is detected by the optical detection device from the adhesive body. If the holding part or at least the holding portion is made of glass, an at least partially translucent plastics material, or another translucent material, it may be sufficient to take a photo of the adhesive body from the outside of the holding part of the hollow needle or cannula and the holding part. The components or component portions to be picked up can be illuminated by at least one light source.

In a development of the invention, it is provided that the adhesive body or the adhesive forming the adhesive body consists at least partially of a fluorescent material and/or contains fluorescent particles. If the fluorescent material or the fluorescent particles are excited by illumination, for example, before being detected by the detection device, they glow for a short period of time and in this way stand out clearly from neighboring components, as a result of which they can be photo-detected with high accuracy.

Provision is preferably made for the adhesive body to be illuminated by an illumination device with at least one light source before and/or during and/or after detection by means of the optical detection device. The adhesive body is preferably illuminated with light having a wavelength of $\leq 500$ nm and in particular with light having a wavelength of $\leq 405$ nm. It has proven advantageous to illuminate the adhesive body with light having a wavelength in the range from 360 nm to 370 nm.

At least one light-emitting diode (LED) can be used as the light source.

A commercially available, preferably high-resolution camera can be used as the camera, with which very short exposure sides in the range from 20 μs to 1 s should also be possible.

If the holding part is made of glass or another highly reflective material, there is a risk that light reflections will form on the surface of the holding part, which light reflections will also be detected by the optical detection device and can interfere with the evaluation. It is therefore preferably provided that the image data relating to regions of the holding part in which strong light reflections can occur are disregarded in the evaluation. This can be achieved by the evaluation unit segmenting the recorded image data into different image regions and in particular hiding those regions for the evaluation, in which regions either light reflections are detected and/or it is known that light reflections frequently occur there.

During image processing, the image can also be prepared with "binning" in order to increase the brightness values of the camera resolution. In the case of "binning," the brightness values of a specific number of neighboring pixels are added up and those pixels combined into one pixel. This makes a weak fluorescence of the material of the adhesive body more visible.

In order to determine highly reflective regions of the holding part and/or the hollow needle or cannula, it can be provided to detect a holding part and a hollow needle or cannula in a preceding method step, without detecting an adhesive body and evaluating the corresponding photos. This makes it possible to determine image regions in which the light is reflected and which are not due to the luminosity of the adhesive body, since no adhesive body is present at this point. The determined regions of reflection are preferably disregarded or hidden during the evaluation of the image data of the holding part with the adhesive body and with the hollow needle or cannula. In this way, those image regions that are used for the evaluation can be determined.

If the holding part is tubular and the hollow needle or cannula is inserted from one axial end into the interior space of the tubular holding part, the light source can be arranged on the axially opposite side of the holding part, so that it can be provided that the adhesive body is illuminated through the interior space of the holding part. Due to the introduction of the light through the interior space of the holding part, reflections can be reduced. The fewer reflections there are, the better the relatively weak fluorescence of the adhesive body can be detected. For this reason, other external, disruptive light sources should preferably also be shielded.

Alternatively or additionally, it can be provided that the adhesive body is illuminated through the material of the holding part.

In a possible embodiment of the invention, it can be provided that the adhesive forming the adhesive body is an adhesive that hardens under light. In this way, it is possible to combine the hardening of the adhesive and the illumination of the adhesive body for detection by the optical detection device. In particular, it can be provided that the hardening of the adhesive takes place at least partially and preferably completely synchronously with the illumination of the adhesive body by the light source.

In a possible embodiment of the invention, it can be provided that the adhesive is first pre-hardened. This can be done by applying light by means of an upstream 1st light source, whereby the adhesive is additionally charged with light energy. After pre-hardening the adhesive, the adhesive body is detected by means of the optical detection device, wherein, during detection, the 1st light source and/or a 2nd light source preferably remain switched on or are reduced to a reduced output. In the case of the power reduction of the 1st and/or 2nd light source, it can be achieved that the light emitted by the 1st and/or 2nd light source and any resulting light reflections do not affect the detection of the adhesive body by the optical detection device.

The pre-hardening and the optical detection of the adhesive body can take place in a common work station. However, it is also possible to carry out the previous pre-hardening and the optical detection of the adhesive body in separate work stations one after the other or simultaneously or with a lateral overlap. For pre-hardening, the adhesive body can be illuminated for a period of 1 s to 6 s.

As soon as the detection of the adhesive body by the optical detection device is complete, the adhesive is hardened, for example by activating the 1st and/or 2nd light source and/or another 3rd light source and exposing the adhesive body to the light and thereby hardening it.

In a preferred embodiment of the invention, it is provided that at least the optical detection of the adhesive body is carried out in a darkroom. A darkroom is understood to mean a room surrounded by walls that is shielded from external light. The darkroom can have a preferably closable entrance opening and/or a preferably closable exit opening. A test body, which comprises the holding part, the hollow needle or cannula, and the adhesive body, is placed in the darkroom and is shielded there from external light. The test body is positioned in the desired way and then the corresponding light source is activated. The image is then recorded with an exposure time of preferably 0.01 s with 0.02 s. The light source is preferably switched on before the image is recorded and only switched off again after the image has been recorded, it being possible for the light source to be activated for a period of, for example, 0.1 s to 0.8 s and preferably 0.5 s.

The adhesive body can also be pre-hardened in the darkroom, but it is also possible to carry out the pre-hardening outside of the darkroom, i.e. before the test body enters the darkroom.

The subsequent hardening of the adhesive body can also take place in the darkroom, i.e. before the test body is preferably driven out of the darkroom through a closable exit opening. Alternatively, however, it is also possible to carry out the hardening of the adhesive body only after leaving the darkroom.

A device for checking an adhesive connection between a hollow needle or cannula and a holding part is distinguished by an optical detection device, by means of which the adhesive body can be detected. In addition, an evaluation unit is provided, to which data relating to the adhesive body can be supplied by the detection device. The detection device has a camera with which image data of the adhesive body can be generated.

Further features of the device result from the above explanation of the method, it being possible for the device-technical features presented in connection with the method to be provided individually or in any combination with one another.

BRIEF DESCRIPTION OF THE DRAWINGS

Further details and features of the invention are apparent from the following description of an embodiment with reference to the drawings, in which.

5

Figure 2:
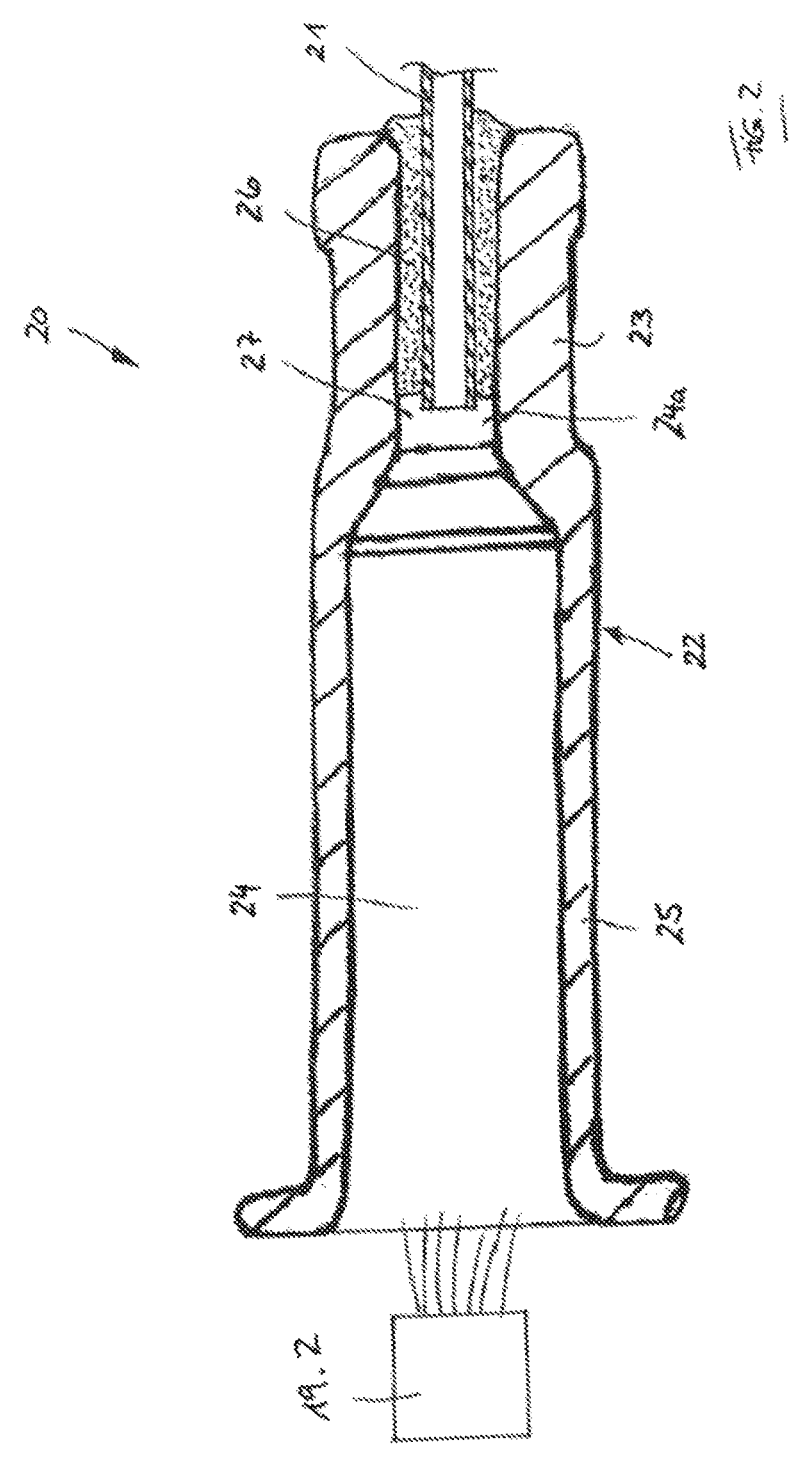
FIG. 2 is a longitudinal section through a test body.
Figure 3:
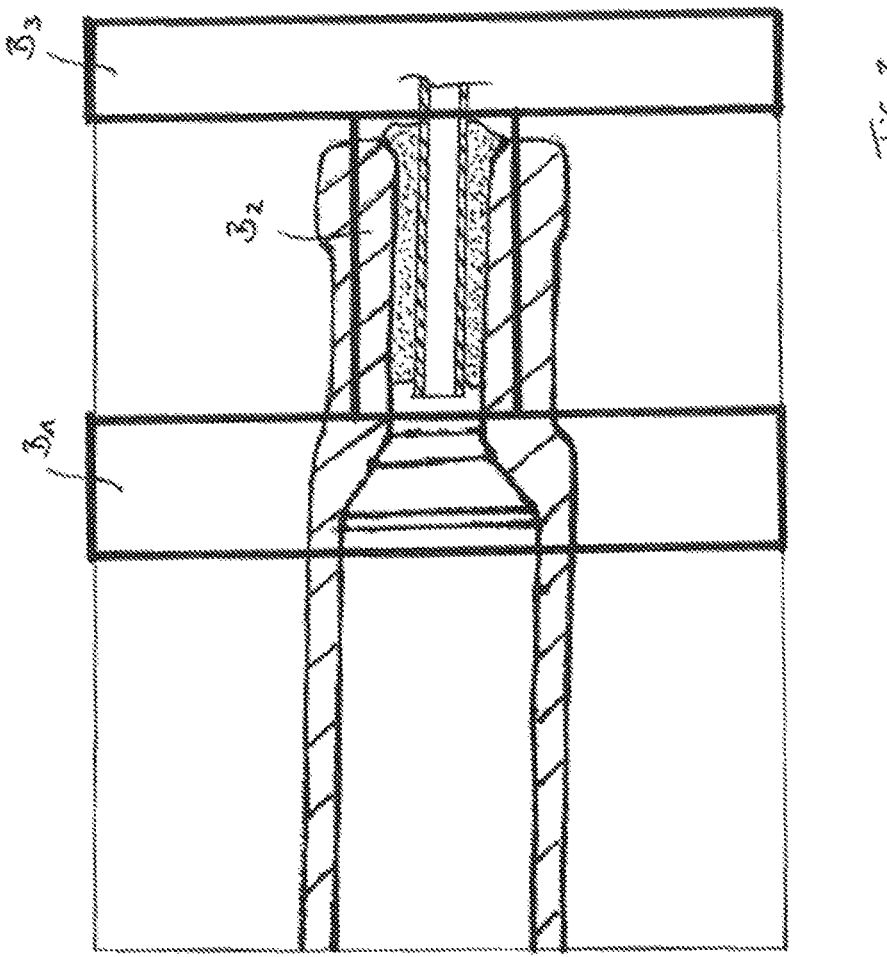

FIG. 3 is a representation corresponding to FIG. 2 with individual image regions.

DETAILED DESCRIPTION

Figure 1:
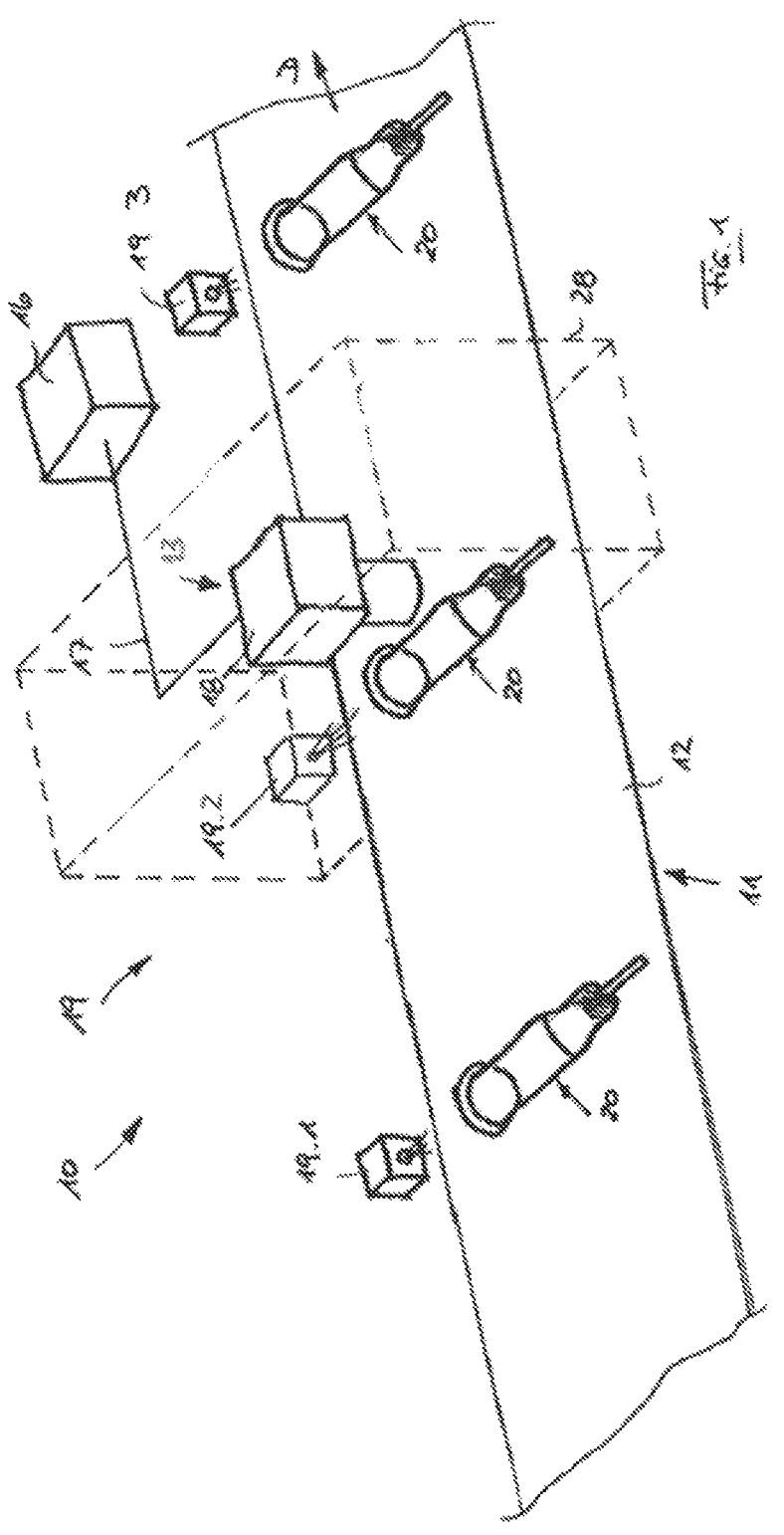
FIG. 1 is a schematic perspective view of a device for checking an adhesive connection.

FIG. 1 shows a device 10 for checking an adhesive connection on test bodies 20. The test bodies 20 lie on a conveying device 11 in the form of a conveyor belt 12 which, according to FIG. 1, is moved to the right, as indicated by the arrow D. On the conveyor belt 12, the test bodies 20 are arranged in a row at a mutual distance and in a predetermined alignment and positioning.

An optical detection device 13 is positioned above the conveyor belt 12. The optical detection device 13 has a camera 18 which can record image data of the test body 20 located below it. The camera 18 is connected to an evaluation unit 16 via a line 17.

A lighting device 19 having a plurality of light sources 19.1, 19.2, 19.3 in the form of light-emitting diodes is arranged to the side of the conveyor belt 12, wherein a 1st light source 19.1 is arranged upstream of the camera 18, and a 3rd light source 19.3 is arranged downstream of the camera 18. A further 2nd light source 19.2 illuminates the test body 20 when it is arranged below the camera 18.

A darkroom 28 is provided, which is indicated only schematically in FIG. 1 and in which the optical detection device 13 and the camera 18 are positioned. The test bodies 20 can enter the darkroom 28 preferably through a closable entrance opening or a lock and are shielded from the environment in the darkroom 28. The 2nd light source 19.2, which illuminates the test body 20 when it is positioned below the camera 18, is also positioned within the darkroom 28. After detection by the optical detection device 13, the test body 20 can preferably exit the darkroom 28 through a closable exit opening or a lock.

FIG. 2 is a longitudinal section through the test body 20. The test body 20 has a holding part 22 made of glass or a transparent plastics material. The holding part 22 is designed to be tubular and has an interior space 24 which extends through the entire axial length of the holding part 22. In the right end region of the holding part 22, as shown in FIG. 2, a holding portion 23 is formed on the holding part. The holding portion 23 is characterized in that the inner dimensions of the interior space 24 are reduced to form a fastening space 24a. In the left end region of the holding part 22 according to FIG. 2, a placement portion 25 is formed thereon, with which placement portion the holding part 22 can be placed, for example, on a syringe body of a medical syringe.

A hollow needle or cannula 21 is inserted in the axial direction into the fastening space 24a with play, so that an intermediate space 27 is formed between the outer surface of the hollow needle or cannula 21 and the inner wall of the fastening space 24a, into which the adhesive forming an adhesive body 26 is filled.

The 2nd light source 19.2 is arranged at the axial end facing away from the hollow needle or cannula 21, i.e. on the left-hand side of the holding part 22 according to FIG. 2, the light of which is directed through the interior space 24 of the holding part 21 onto the adhesive body 26, acts thereon, and hardens it.

FIG. 3 shows an example of an image that is recorded by means of the camera 18 of a part of the test body 20. Individual regions $B_1$ and $B_3$ of the image are disregarded in the evaluation to determine the size or volume of the adhesive body and the determination of the position and configuration of the adhesive body 26, since experience has shown that increased light reflections appear in these regions $B_1$ and $B_3$. Only preferred regions B2, which are determined by the TARGET configuration of the adhesive body 26, are included in the evaluation of the image.

To check the adhesive connection, the test body 20 to be checked is placed on the conveyor belt 12. Shortly before the test body 20 reaches a position below the camera 18, it is subjected to light from the 1st light source 19.1 arranged upstream of the camera 18. As a result, the adhesive forming the adhesive body 26 is pre-hardened. The test body 20 then moves into the darkroom 28.

When the test body 20 to be examined has reached a position below the camera 18, illumination takes place by means of the 2nd light source 19.2, as a result of which the adhesive body 26 is charged with light energy which it then emits again with a time delay in the following, in particular if the adhesive consists at least partly of a fluorescent material or at least contains fluorescent particles. The adhesive body 26 lights up as a result of its fluorescence and can in this way be identified and evaluated with high accuracy on a photo taken by means of the camera 18.

After the detection of the adhesive body 26 by means of the camera 18, the adhesive body 26 is moved out of the darkroom 28 and then, in a position downstream of the camera 18, is subjected again to light of the 3rd light source 19.3, whereby hardening of the adhesive body 26 takes place.

Depending on the evaluation of the image data of the adhesive body 26 detected by means of the camera 18 by the evaluation unit 16, the test body 20 is either approved for further processing or sorted out of the production process as defective.

The invention claimed is:

1. A method for checking an adhesive connection between a hollow needle or cannula and a holding part, wherein the hollow needle or cannula is inserted with play in a holding portion of the holding part, and an intermediate space between the hollow needle or cannula and the holding portion is at least partially filled with an adhesive body, the method comprising detecting the adhesive body by an optical detection device, transmitting data relating to the adhesive body from the detection device to an evaluation unit in which the data are evaluated, wherein the detection device has a camera and the method further includes generating image data of the adhesive body with the camera, determining or calculating an ACTUAL volume and/or an ACTUAL configuration of the adhesive body from the image data of the adhesive body, and comparing the ACTUAL volume and/or the ACTUAL configuration of the adhesive body with a TARGET volume and/or a TARGET configuration of the adhesive body; wherein the adhesive body is illuminated with at least one light source during detection by the detection device; and wherein the adhesive is first pre-hardened, the detection of the adhesive body takes place subsequently by the detection device, and the adhesive is then further hardened.

2. The method according to claim 1, wherein the adhesive body consists at least partially of a fluorescent material and/or contains fluorescent particles.

3. The method according to claim 1, wherein the adhesive body is illuminated with light having a wavelength of ≤500 nm.

4. The method according to claim 3, wherein the adhesive body is illuminated with light having a wavelength of ≤405 nm.

5. The method according to claim 4, wherein the adhesive body is illuminated with light having a wavelength in the range from 360 nm to 370 nm.

6. The method according to claim 1, wherein at least one light-emitting diode (LED) is used as the at least one light source.

7. The method according to claim 1, wherein the adhesive body is illuminated through the holding part.

8. The method according to claim 1, wherein the adhesive forming the adhesive body is an adhesive that hardens under light, and the hardening of the adhesive takes place at least partially synchronously with the illumination of the adhesive body by the at least one light source.

9. The method according to claim 1, wherein the detection of the adhesive body takes place by the detection device in a darkroom.

10. The method according to claim 8, wherein the pre-hardening of the adhesive and/or the hardening of the adhesive takes place in the darkroom.

* * * * *